United States Patent
Oshinski et al.

(10) Patent No.: US 11,642,461 B2
(45) Date of Patent: May 9, 2023

(54) MEDICAL INFUSION PUMP FOR DELIVERY OF A FLUID

(71) Applicant: Becton, Dickinson and Company, Franklin Lakes, NJ (US)

(72) Inventors: Matthew Oshinski, Oak Ridge, NJ (US); Christian Sandmann, Wayne, NJ (US); Timothy Walsh, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/977,936

(22) PCT Filed: Mar. 19, 2019

(86) PCT No.: PCT/US2019/022962
§ 371 (c)(1),
(2) Date: Sep. 3, 2020

(87) PCT Pub. No.: WO2019/183088
PCT Pub. Date: Sep. 26, 2019

(65) Prior Publication Data
US 2021/0085859 A1 Mar. 25, 2021

Related U.S. Application Data

(60) Provisional application No. 62/645,444, filed on Mar. 20, 2018.

(51) Int. Cl.
*A61M 5/168* (2006.01)
*A61M 5/142* (2006.01)
*A61M 5/36* (2006.01)

(52) U.S. Cl.
CPC ........ *A61M 5/16877* (2013.01); *A61M 5/142* (2013.01); *A61M 5/16804* (2013.01); *A61M 5/16831* (2013.01); *A61M 5/365* (2013.01); *A61M 2205/18* (2013.01); *A61M 2205/3334* (2013.01); *A61M 2205/583* (2013.01)

(58) Field of Classification Search
CPC .............. A61M 5/16877; A61M 5/142; A61M 5/16804; A61M 5/16831; A61M 5/365; A61M 5/16809; A61M 5/16813; A61M 5/16886; A61M 5/172; A61M 2205/3331;
(Continued)

(56) References Cited

U.S. PATENT DOCUMENTS 4,150,672 A * 4/1979 Whitney ............. A61M 5/1422
604/246
4,822,344 A * 4/1989 O'Boyle ........... A61M 5/16881
D24/111
(Continued)

FOREIGN PATENT DOCUMENTS

EP 0296124 A2 12/1988
EP 3388095 A1 10/2018
(Continued)

*Primary Examiner* — Nathan R Price
*Assistant Examiner* — Anna E Goldberg-Richmeier
(74) *Attorney, Agent, or Firm* — The Webb Law Firm

(57) ABSTRACT

An infusion pump (18) for delivery of a fluid is disclosed. The infusion pump allows a user to selectively control a flow rate of a fluid and includes a spike member (26) that is connectable to an injection port of an intravenous fluid container (12).

18 Claims, 17 Drawing Sheets

(58) Field of Classification Search
CPC .... A61M 2205/3334; A61M 2205/583; A61M 2205/587; A61M 2205/18
See application file for complete search history.

(56) References Cited

U.S. PATENT DOCUMENTS

| | | | | |
|---|---|---|---|---|
| 2008/0098798 | A1* | 5/2008 | Riley | A61M 5/365 |
| | | | | 73/19.03 |
| 2011/0264053 | A1* | 10/2011 | Nilsson | A61M 5/141 |
| | | | | 604/247 |
| 2012/0283632 | A1* | 11/2012 | Svensson | A61M 5/1411 |
| | | | | 604/67 |
| 2016/0058940 | A1 | 3/2016 | Zhang et al. | |
| 2016/0144148 | A1* | 5/2016 | Crone | G16H 40/63 |
| | | | | 128/203.14 |
| 2018/0014382 | A1 | 1/2018 | Glaser et al. | |

FOREIGN PATENT DOCUMENTS

| | | | |
|---|---|---|---|
| JP | 2016187591 A | | 11/2016 |
| KR | 20170124826 A | * | 11/2017 |
| WO | 8200590 A2 | | 3/1982 |
| WO | 9215349 A1 | | 9/1992 |
| WO | 2017159683 A1 | | 9/2017 |

* cited by examiner

MEDICAL INFUSION PUMP FOR DELIVERY OF A FLUID

CROSS-REFERENCE TO RELATED APPLICATION

This application is the United States national phase of International Application No. PCT/US2019/022962 filed Mar. 19, 2019, and claims priority to U.S. Provisional Application Ser. No. 62/645,444, entitled "Medical Infusion Pump for Delivery of a Fluid", filed Mar. 20, 2018, the disclosures of which are hereby incorporated by reference in their entirety.

BACKGROUND OF THE INVENTION

1. Field of the Disclosure

The present disclosure relates generally to a medical infusion pump for the delivery of a fluid. More particularly, the present disclosure relates to a small micropump that replaces a drip chamber in a conventional intravenous (IV) set.

2. Description of the Related Art

The administration of medicines, rehydration fluids and nutritional formulations by intravenous (IV) infusion is one of the most common medical procedures. In gravity drip IV infusion, an IV bag is placed above the level of the patient, with gravity causing IV fluid to flow out from the IV bag. Gravity infusion sets are used for the administration of rehydration fluids, non-critical therapeutic treatments, and drug administration. Gravity based IV sets require a patient to be close to an IV pole for the duration of the infusion.

SUMMARY OF THE INVENTION

The present disclosure is directed to an infusion pump for delivery of a fluid. The infusion pump allows a user to selectively control a flow rate of a fluid and includes a spike member that is connectable to an injection port of an intravenous fluid container.

The infusion pump of the present disclosure replaces a drip chamber in a conventional intravenous (IV) set. Advantageously, integrating an infusion pump of the present disclosure into an IV set increases a patient's mobility while receiving an IV. Early ambulation after a hospital procedure is known to have many benefits and contributes to improved patient outcomes. By having an infusion pump of the present disclosure integrated into an IV set, a patient can be freed from the burden of bringing an IV pole along with them as they ambulate. Common infusions are gravity based, and thus a patient is required to be close to the IV pole for the duration of the infusion. An infusion pump of the present disclosure allows a patient to be able to wear a small IV bag on their arm, for example, or carry the IV bag and pump in a small backpack. The active fluid delivery of the infusion pump of the present disclosure allows for orientation independence, i.e., the system is not in any way dependent on gravity for the delivery of fluid so the bag need not be above the pump or the patient's catheter. The patient could wear the bag on an arm and freely lie down or get up and walk around with no interruption in the infusion. In this manner, a patient would be free to move about unencumbered by an IV pole.

In accordance with an embodiment of the present invention, an infusion pump for delivery of a fluid includes a housing having an inlet and an outlet; a spike member at the inlet, the spike member defining a portion of a fluid channel, the fluid channel in fluid communication with the inlet and the outlet; a drive system for pumping the fluid through the spike member and out the outlet of the housing; and a controller in communication with the drive system, wherein the controller selectively controls a flow rate of the fluid.

In one configuration, the infusion pump includes a flow rate indicator. In another configuration, the flow rate indicator includes a first LED element providing a first visual indication and a second LED element providing a second visual indication different than the first visual indication. In yet another configuration, the infusion pump includes a flow rate selector button that allows a user to select the flow rate of the fluid. In one configuration, the infusion pump includes an alarm system for detecting air within the infusion pump. In another configuration, the alarm system includes a sensor. In yet another configuration, the infusion pump includes a strap receiving loop. In one configuration, the infusion pump includes a flexible tubing removably connectable to the outlet of the housing. In another configuration, the infusion pump includes a light bar, wherein the light bar includes a scrolling LED element that is activated when the infusion pump is running. In yet another configuration, the inlet of the housing includes a recessed portion, wherein a portion of the spike member is disposed within the recessed portion. In one configuration, the spike member is connectable to an injection port of an intravenous fluid container.

In accordance with another embodiment of the present invention, a medical infusion system includes an intravenous fluid container having an injection port; and an infusion pump for delivery of a fluid, comprising: a housing having an inlet and an outlet; a spike member at the inlet, the spike member defining a portion of a fluid channel, the fluid channel in fluid communication with the inlet and the outlet; a drive system for pumping the fluid through the spike member and out the outlet of the housing; and a controller in communication with the drive system, wherein the controller selectively controls a flow rate of the fluid, wherein the spike member is connectable to the injection port.

In one configuration, the infusion pump includes a flow rate indicator. In another configuration, the flow rate indicator includes a first LED element providing a first visual indication and a second LED element providing a second visual indication different than the first visual indication. In yet another configuration, the flow rate indicator includes a plurality of different flow rate elements. In one configuration, the first LED element is activated when a particular flow rate element is selected. In another configuration, the infusion pump includes an alarm system for detecting air within the infusion pump. In yet another configuration, the alarm system includes a sensor. In one configuration, when the sensor detects the presence of air, the second LED element is activated. In another configuration, the infusion pump includes a flow rate selector button that allows a user to select the flow rate of the fluid. In yet another configuration, the infusion pump includes a strap receiving loop. In one configuration, the medical infusion system is disposable. In another configuration, the fluid is within the intravenous fluid container. In yet another configuration, the fluid comprises a medicament. In one configuration, the medical infusion system includes a flexible tubing removably connectable to the outlet of the housing. In another configuration, the medical infusion system includes a light bar, wherein the light bar includes a scrolling LED element that is activated when the infusion pump is running. In yet another configuration, the housing includes a finger grasping lip portion adjacent the inlet. In one configuration, the inlet of the housing includes a recessed portion, wherein a portion of the spike member is disposed within the recessed portion.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
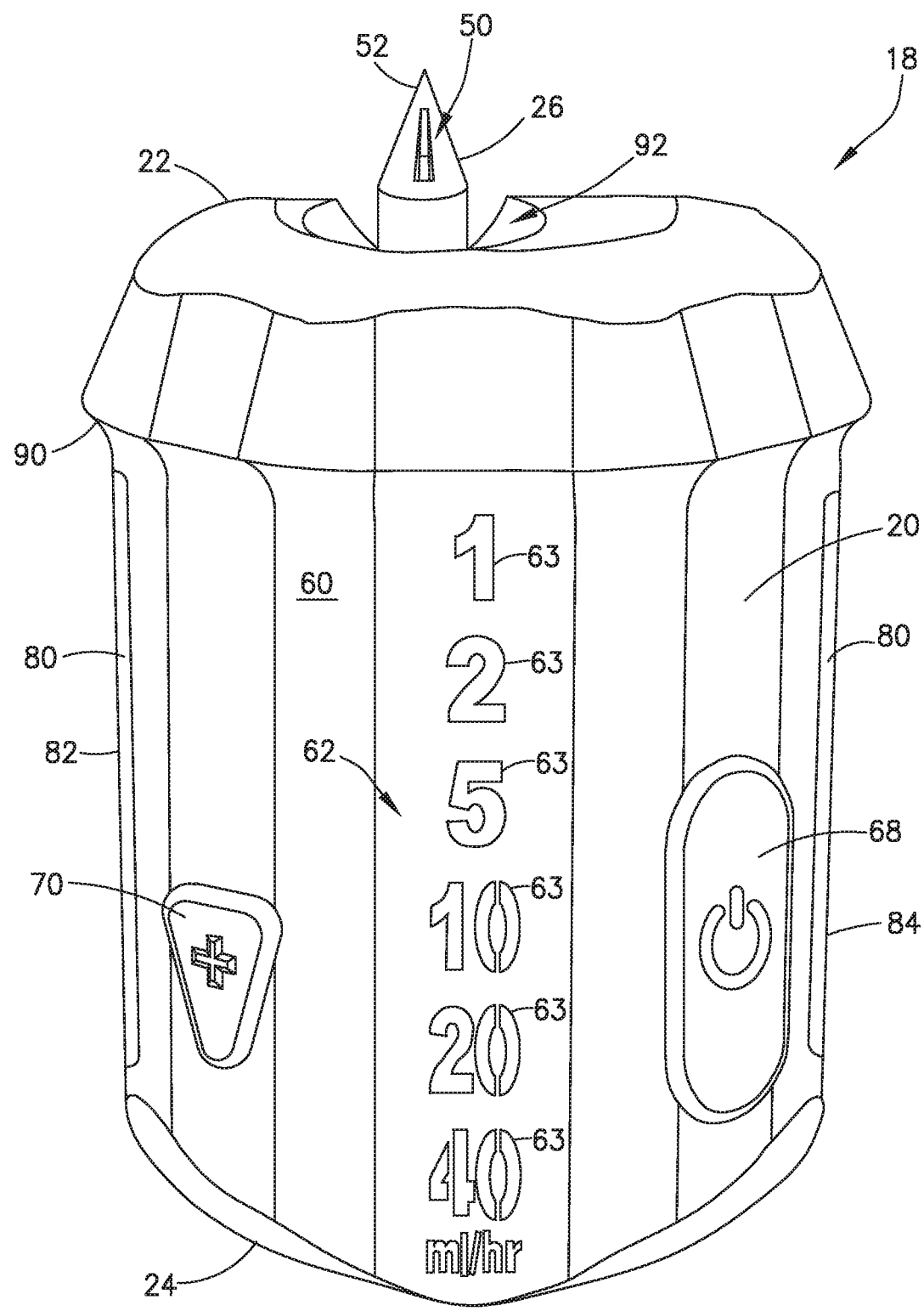
FIG. 1 is a front perspective view of an infusion pump in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof, shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to an infusion pump 18 for delivery of a fluid. The infusion pump allows a user to selectively control a flow rate of a fluid and includes a spike member that is connectable to an injection port of an intravenous fluid container.

The infusion pump of the present disclosure replaces a drip chamber in a conventional intravenous (IV) set. Advantageously, integrating an infusion pump of the present disclosure into an IV set increases a patient's mobility while receiving an IV. Early ambulation after a hospital procedure is known to have many benefits and contributes to improved patient outcomes. By having an infusion pump of the present disclosure integrated into an IV set, a patient can be freed from the burden of bringing an IV pole along with them as they ambulate. Common infusions are gravity based, and thus a patient is required to be close to the IV pole for the duration of the infusion. An infusion pump of the present disclosure allows a patient to be able to wear a small IV bag on their arm for example, or carry the IV bag and pump in a small backpack. The active fluid delivery of the infusion pump of the present disclosure allows for orientation independence, i.e., the system is not in any way dependent on gravity for the delivery of fluid so the bag need not be above the pump or the patient's catheter. The patient could wear the bag on an arm and freely lie down or get up and walk around with no interruption in the infusion. In this manner, a patient would be free to move about unencumbered by an IV pole.

In one embodiment, the infusion pump 18 of the present disclosure may be part of a medical infusion system. For example, in an exemplary embodiment, a medical infusion system 10 of the present disclosure includes an intravenous fluid container or bag 12 having an injection port 14 and the micropump or infusion pump 18 for delivery of a fluid 16.

In one embodiment, a fluid 16 is contained within the intravenous fluid container 12.

Referring to FIGS. 1-7A, 7C-10, and 14, an infusion pump 18 of the present disclosure generally includes a housing 20 having an inlet, first end or an inlet end 22 and an outlet, a second end or outlet end 24, a spike member or anchor member 26 at the inlet 22, a drive system 28 for pumping a fluid 16 through the spike member 26 and out the outlet 24 of the housing 20, and a processor or controller 30 in communication with the drive system 28. In one embodiment, the controller 30 selectively controls a flow rate of the fluid 16 being delivered through the infusion pump 18. In one embodiment, the inlet 22 may be located at a top portion of the housing 20 and the outlet 24 may be located at a bottom portion of the housing 20. It is contemplated that other configurations of the inlet 22 and the outlet 24 may be used in accordance with the present disclosure. For example, in one embodiment, the inlet 22 may be located at a top portion of the housing 20 and the outlet 24 may be located at a side portion of the housing 20. In another embodiment, the inlet 22 may be located at a side portion of the housing 20 and the outlet 24 may be located at an opposite side portion of the housing 20, or any other configurations of the inlet 22 and the outlet 24 are possible.

Importantly, the micropump or infusion pump 18 of the present disclosure is small, i.e., the infusion pump 18 of the present disclosure is smaller than conventional large volume smart pumps. In one exemplary embodiment, the infusion pump 18 of the present disclosure is approximately 2.8 inches tall. In one exemplary embodiment, the infusion pump 18 of the present disclosure is approximately 1.8 inches wide. In one exemplary embodiment, the infusion pump 18 of the present disclosure is approximately 1.0 inches deep. However, it is contemplated an infusion pump 18 of the present disclosure may have other dimensions and function as described herein.

In one embodiment, the infusion pump 18 of the present disclosure may be part of a medical infusion system 10 including an intravenous fluid container 12. In one exemplary embodiment, referring to FIGS. 6A and 6B, the intravenous fluid container 12 includes at least one injection port 14 having a fluid barrier member 110 and interior walls 112. In one embodiment, the intravenous fluid container 12 may also include additional injection ports 14 having a fluid barrier member 110 and interior walls 112. In one embodiment, the intravenous fluid container 12 contains a fluid 16 that is a medicament.

In one embodiment, the inlet end 22 of the infusion pump 18 is connectable to an injection port 14 of the intravenous fluid container 12 such that a fluid 16 within the intravenous fluid container 12 can be delivered to a patient via the infusion pump 18. In one embodiment, the spike member 26 is connectable to the injection port 14 of the intravenous fluid container 12. In one embodiment, the outlet end 24 of the infusion pump 18 is connectable to a flexible tubing or intravenous line 32. The flexible tubing 32 includes a first end 34 connectable to the outlet end 24 of the infusion pump 18 and an opposite second end 36 having a fitting or connector 38. The fitting 38 is connectable to a patient's intravenous port for an infusion transfer of the fluid 16 from the intravenous fluid container 12 to the patient via the infusion pump 18.

In one embodiment, the flexible tubing 32 is removably connectable to the second end 24 of the housing 20 of the infusion pump 18. For example, the flexible tubing 32 may be removably connectable to the second end 24 of the housing 20 of the infusion pump 18 via a Luer lock connection. In another embodiment, the flexible tubing 32 is fixedly connected to the second end 24 of the housing 20 of the infusion pump 18. For example, in one embodiment, the flexible tubing 32 is integral with the second end 24 of the housing 20 of the infusion pump 18.

The infusion pump 18 of the present disclosure replaces a drip chamber in a conventional intravenous (IV) set. Referring to FIG. 7B, a conventional intravenous set 100 having a drip chamber 102 is illustrated. Advantageously, integrating an infusion pump 18 of the present disclosure into an intravenous set, e.g., a medical infusion system 10, increases a patient's mobility while receiving an IV. Early ambulation after a hospital procedure is known to have many benefits and contributes to improved patient outcomes. By having an infusion pump 18 of the present disclosure integrated into an intravenous set, e.g., a medical infusion system 10, a patient can be freed from the burden of bringing an intravenous pole 104 (FIG. 7B) along with them as they ambulate. Common infusions are gravity based, and thus a patient is required to be close to the intravenous pole 104 for the duration of the infusion.

Figure 7A:
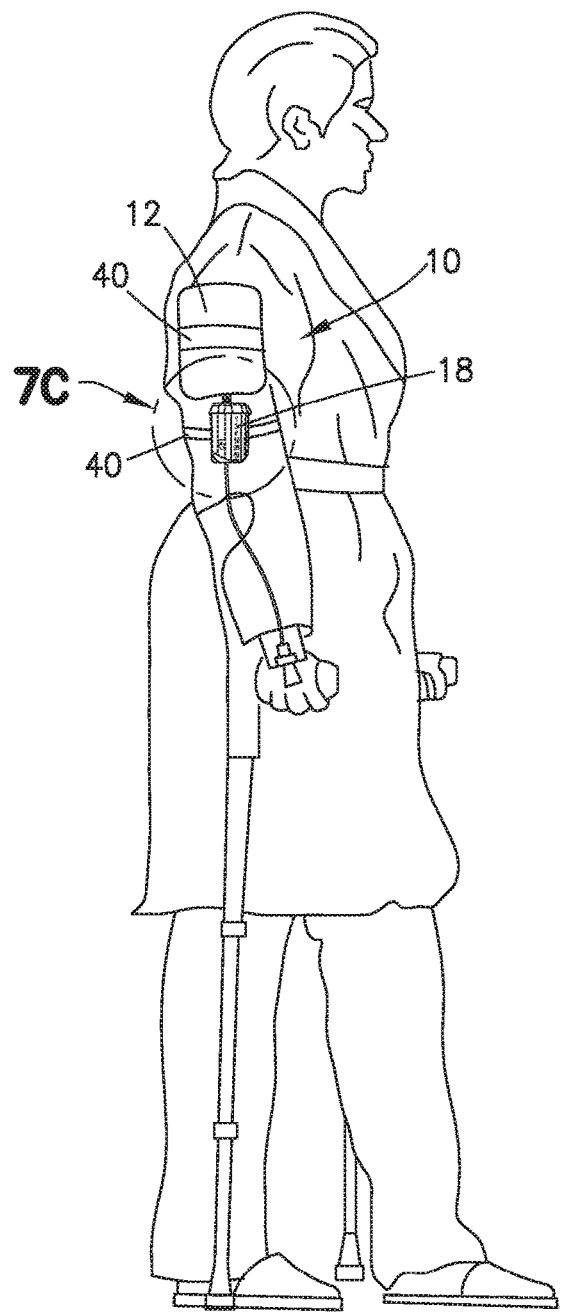
FIG. 7A is a perspective view of a patient wearing a medical infusion system of the present disclosure on their arm via a carrying strap in accordance with an embodiment of the present invention.
Figure 7B:
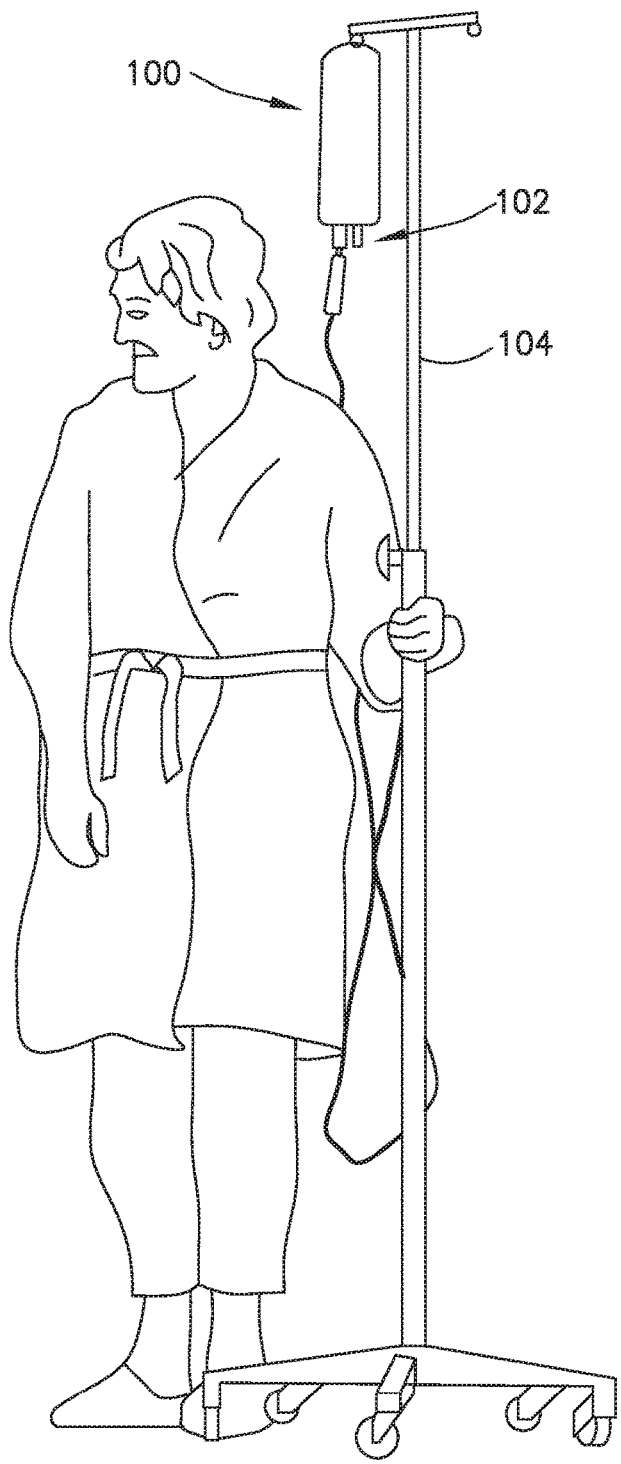
FIG. 7B is a perspective view of a patient using a conventional intravenous set having a drip chamber and intravenous pole.
Figure 7C:
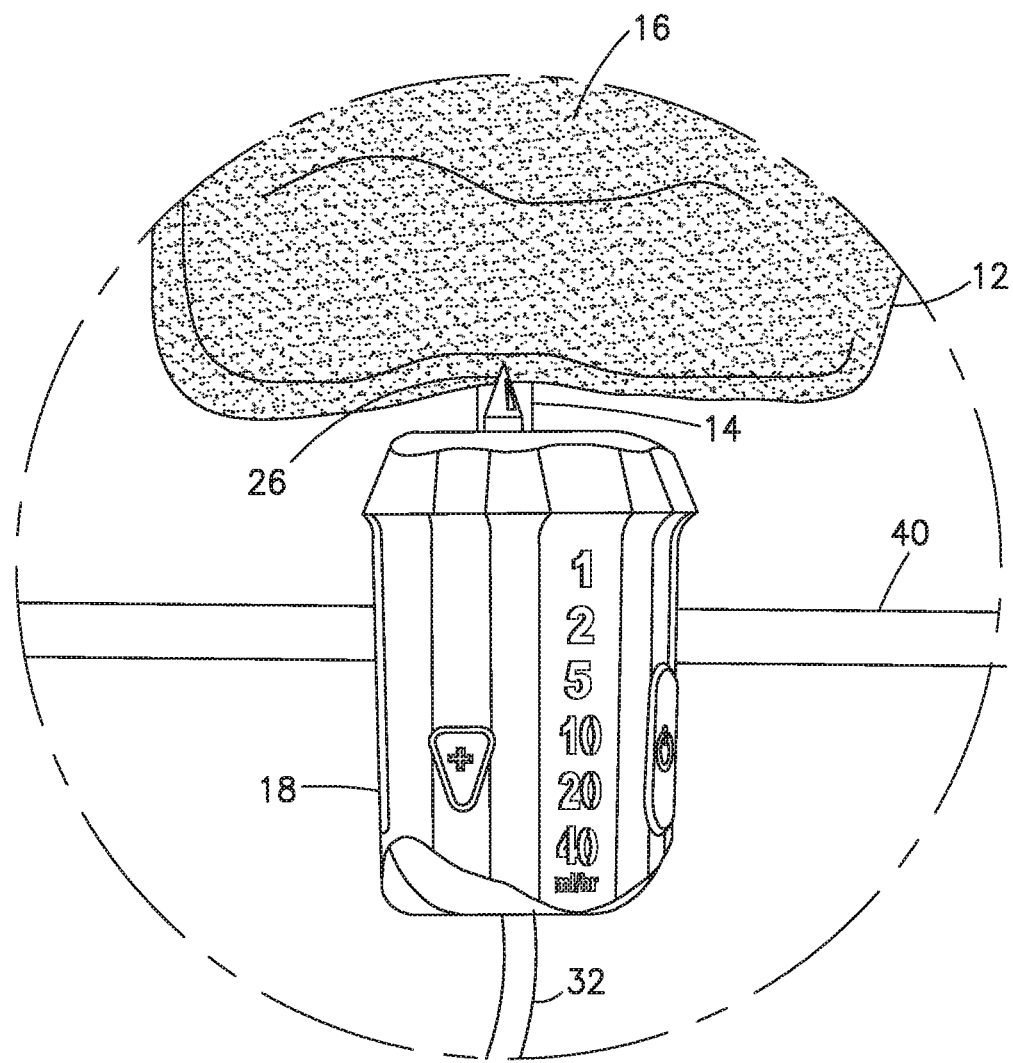
FIG. 7C is an enlarged partial view of an intravenous fluid container, an infusion pump, and a carrying strap taken along a section of FIG. 7A in accordance with an embodiment of the present invention.

Referring to FIG. 7A, an infusion pump 18 and medical infusion system 10 of the present disclosure allows a patient to be able to wear an intravenous fluid container or bag 12 on their arm, for example, or carry the intravenous fluid container 12 and infusion pump 18 in a small backpack. Referring to FIG. 7A, in one embodiment, the infusion pump 18 and medical infusion system 10 of the present disclosure allows a patient to be able to wear an intravenous fluid container or bag 12 on their arm via a carrying strap 40.

The active fluid delivery that the infusion pump 18 and medical infusion system 10 of the present disclosure provides allows for orientation independence, i.e., the medical infusion system 10 of the present disclosure is not in any way dependent on gravity for the delivery of a fluid 16, so the intravenous fluid container 12 does not need to be above the infusion pump 18 or the patient's catheter. The patient could wear the intravenous fluid container or bag 12 on an arm, as described above, and freely lie down or get up and walk around with no interruption in the infusion of the fluid 16. In this manner, a patient would be free to move about unencumbered by an intravenous pole 104 (FIG. 7B).

In one embodiment, the spike member 26 of the infusion pump 18 defines a portion of a fluid channel 50. The fluid channel 50 of the spike member 26 is in fluid communication with the inlet 22 and the outlet 24 of the housing 20 of the infusion pump 18 such that a fluid 16 can be delivered through the fluid channel 50 and out the outlet 24 of the housing 20 to a patient. For example, in one exemplary embodiment, a fluid 16 is drawn in through the fluid channel 50 of the spike member 26 into a tube or fluid channel which carries the fluid 16 to the pump or drive system 28 of the infusion pump 18. The fluid 16 then travels through the drive system 28 of the infusion pump 18 and through the tube or fluid channel to the outlet 24. During travel of the fluid 16 to and out the outlet 24, a pressure sensor may be in line but out of constant fluid flow. In one embodiment, the drive system 28 of the infusion pump 18 may include polyether ether ketone (PEEK) and/or stainless steel components.

Figure 6A:
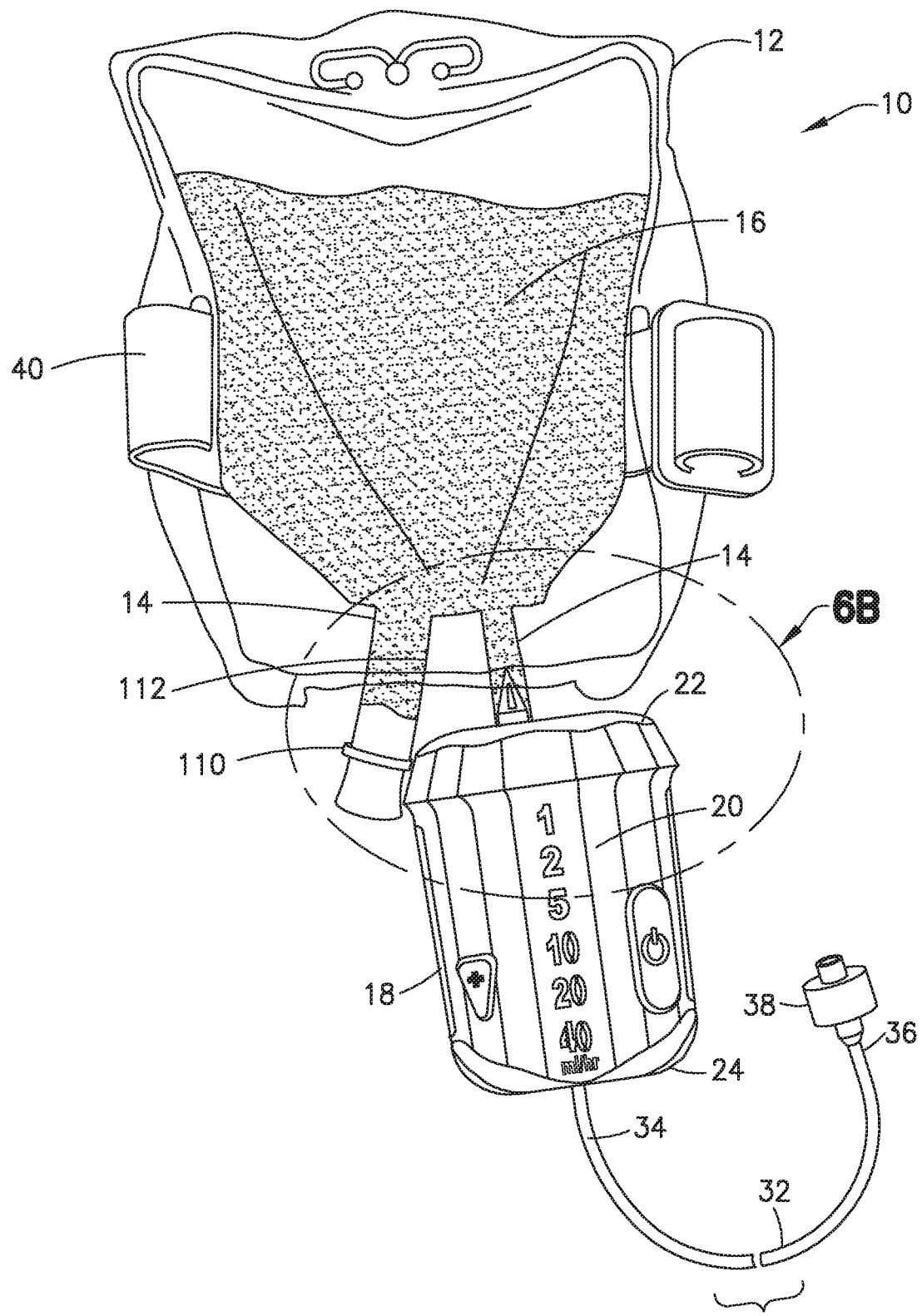
FIG. 6A is a perspective view of a medical infusion system including an intravenous fluid container, a fluid contained within the intravenous fluid container, an infusion pump, and a flexible tubing in accordance with an embodiment of the present invention.
Figure 6B:
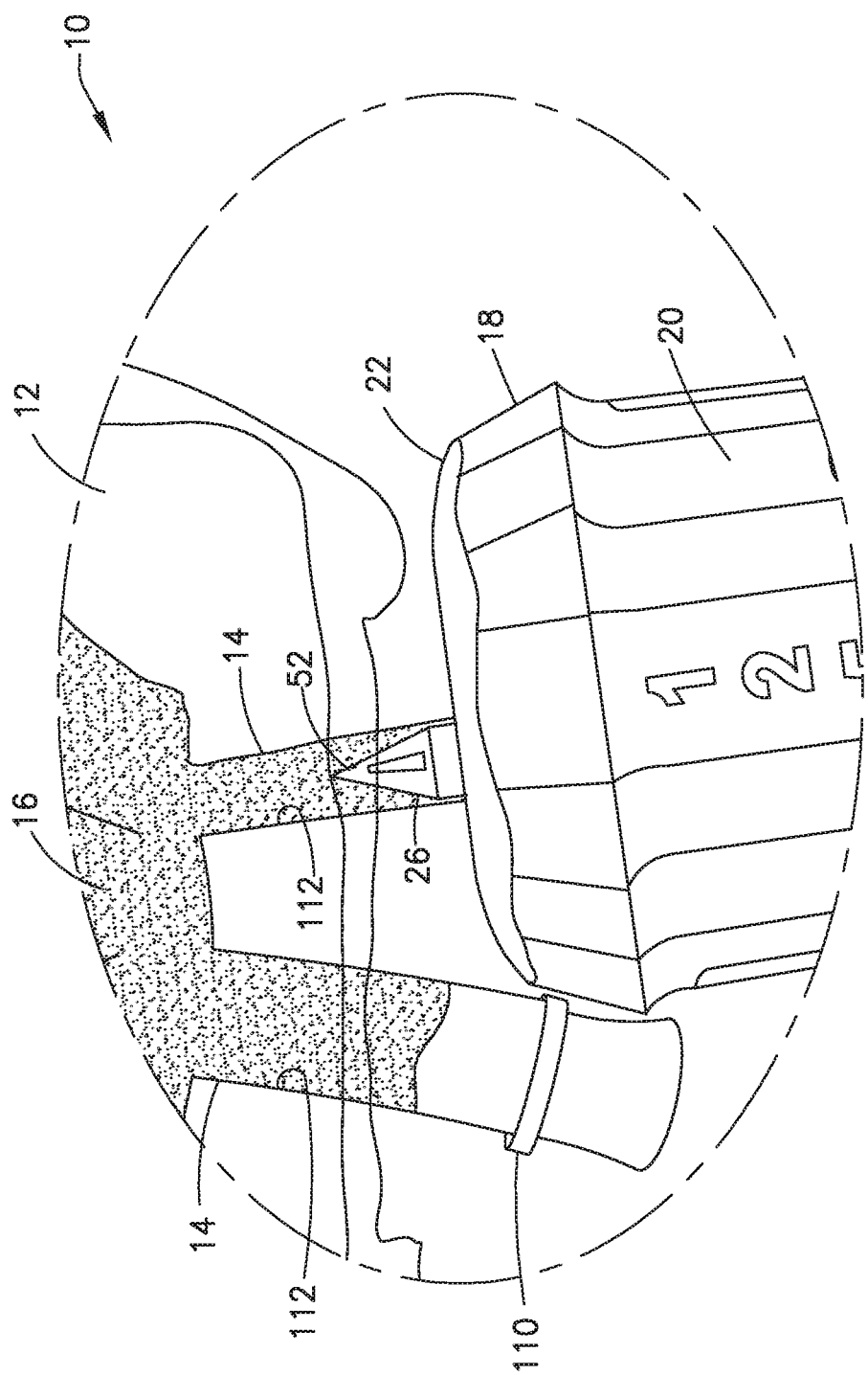
FIG. 6B is an enlarged partial view of the connection between a spike member of an infusion pump and an injection port of an intravenous fluid container taken along a section of FIG. 6A in accordance with an embodiment of the present invention.

As described above, the spike member 26 is connectable to the injection port 14 of the intravenous fluid container 12. For example, the spike member 26 includes a puncturing point 52. Referring to FIGS. 6A and 6B, when a fluid infusion treatment is needed, a patient or a medical practitioner is able to spike or pierce a fluid barrier member 110 of an injection port 14 of intravenous fluid container 12 with puncturing point 52 of spike member 26. Advantageously, the spike member 26 of infusion pump 18 of the present disclosure locks spike member 26 of the infusion pump 18 within an injection port 14 of intravenous fluid container 12, i.e., significant relative movement between spike member 26 of infusion pump 18 and injection port 14 of intravenous fluid container 12 is prevented and disconnection of spike member 26 of infusion pump 18 from injection port 14 of the intravenous fluid container 12 is prevented. In this manner, spike member 26 prevents inadvertent and accidental removal of infusion pump 18 from intravenous fluid container 12 and provides a leakproof connection between infusion pump 18 and intravenous fluid container 12 during an intravenous fluid infusion procedure.

In one embodiment, the spike member 26 may also include an anchor element. For example, the spike member 26 may include a threaded portion. The anchor element or threaded portion allows for the spike member 26 to engage and interface the interior walls 112 of an injection port 14 of intravenous fluid container 12 when connecting infusion pump 18 to an intravenous fluid container 12. In one embodiment, the threaded portion may self-tap and cut its own thread in the interior walls 112 of injection port 14. In this manner, spike member 26 of infusion pump 18 is locked and anchored within injection port 14, i.e., significant relative movement between spike member 26 of infusion pump 18 and injection port 14 of intravenous fluid container 12 is prevented and disconnection of spike member 26 of infusion pump 18 from the injection port 14 of intravenous fluid container 12 is prevented.

Figure 5:
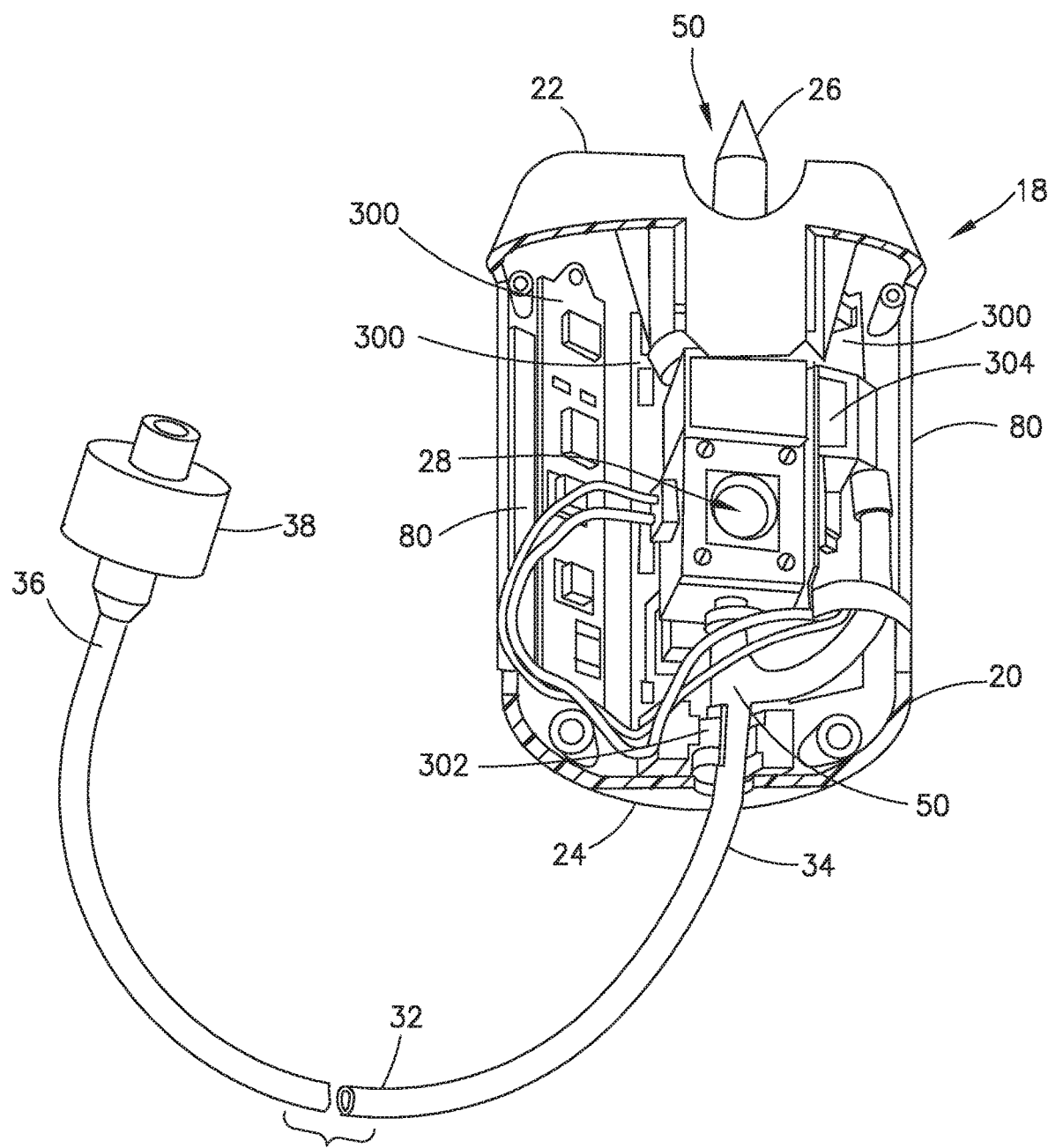
FIG. 5 is a perspective view of an infusion pump and flexible tubing, with a portion of the infusion pump cut-away showing an interior of the infusion pump in accordance with an embodiment of the present invention.

FIG. 5 depicts the interior of an infusion pump 18 in accordance with an exemplary embodiment of the present disclosure. As shown in FIG. 5, the infusion pump 18 includes the housing 20, the drive system 28, a running light bar 80, a circuit board 300, a bubble sensor 302, and a pressure sensor 304.

In one embodiment, the drive system 28 includes a motor. The motor can comprise any electric motor known in the art, including, but not limited to, a brushed direct current (DC) electric motor, a brushless motor, a stepper motor, a servomotor, a gear motor, a hollow shaft motor, or a shaftless motor. In operation, when the motor is actuated, the driving system 28 causes rotary or reciprocal motion within a pump head. The rotary or reciprocal motion within the pump head causes the displacement of fluid along a fluid path. In one exemplary embodiment, the infusion pump 18 may be a micro diaphragm pump using a piezoelectric crystal to drive it. The piezoelectric effect, which converts an applied electrical field into mechanical strain, generates pressure in the pump chamber. Alternating the supplied voltage to the piezoelectric crystal moves a silicon membrane up or down, which in turn draws in fluid through a one-way valve and compresses it in the pump chamber before expelling it through a one-way valve at the exit.

Figure 14:
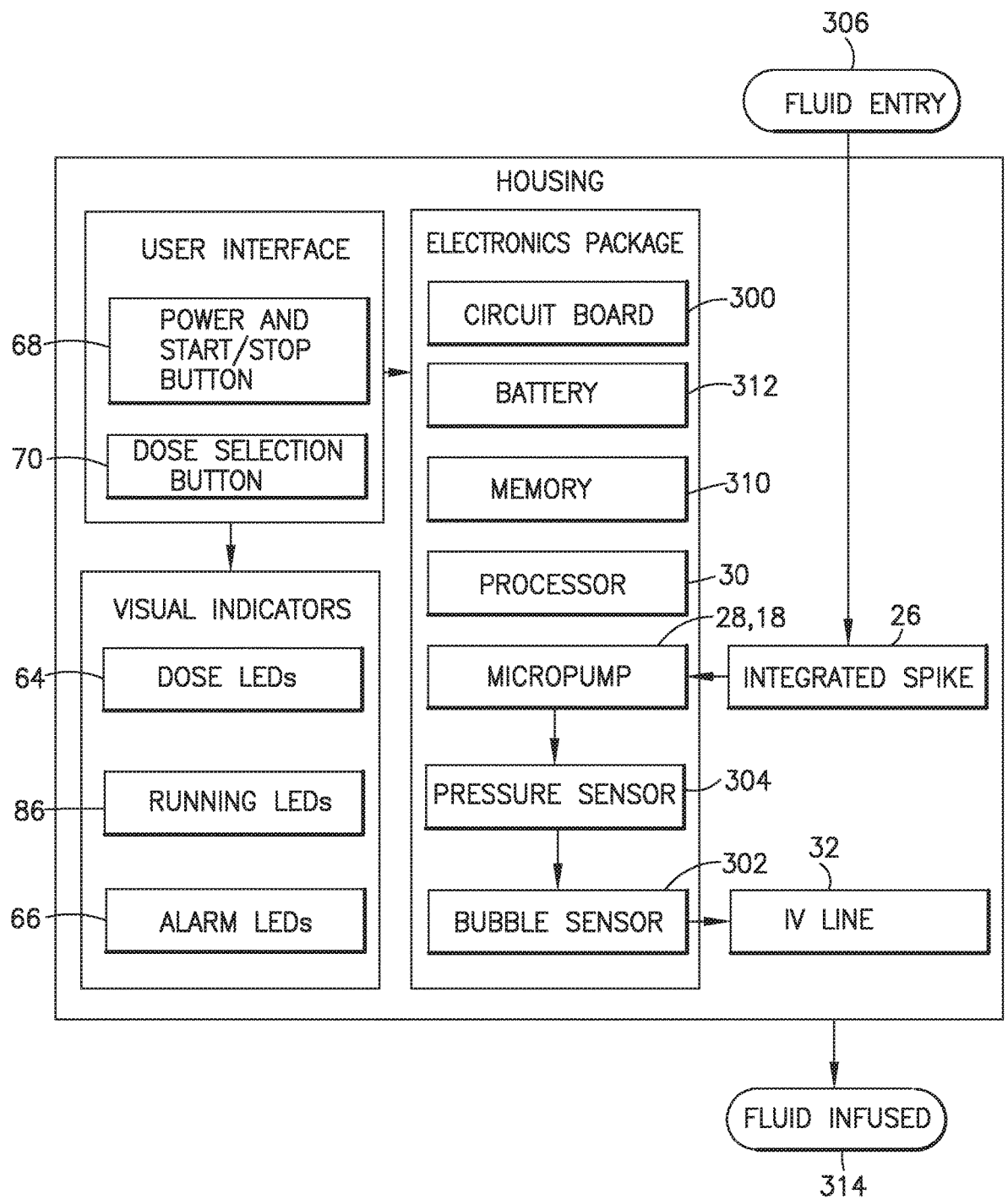
FIG. 14 is a schematic view of an infusion pump in accordance with an embodiment of the present invention.

FIG. 14 depicts a schematic view of the infusion pump 18. The infusion pump 18 includes a fluid entry location 306, a spike member 26, a circuit board 300, a bubble sensor 302, a pressure sensor 304, a micropump 18, a drive system 28, a processor or controller 30, a power button 68, a flow rate selector button 70, a first light-emitting diode (LED) element 64, a second LED element 66, a scrolling LED element 86, a memory 310, a battery 312, a flexible tubing or IV line 32, and a fluid infused location 314.

Referring to FIG. 1, the infusion pump 18 includes a flow rate indicator 62. In one embodiment, a front portion 60 of the infusion pump 18 includes the flow rate indicator 62. In other embodiments, other portions of the infusion pump 18 may include the flow rate indicator 62.

In one embodiment, the flow rate indicator 62 includes a plurality of numbers, e.g., a plurality of different flow rate elements 63, that indicate a selected fluid flow rate through the medical infusion system 10 via infusion pump 18. For example, referring to FIG. 1, the flow rate indicator 62 may include flow rate elements 63 that indicate flow rates of 1, 2, 5, 10, 20, and 40. In one embodiment, the flow rates are provided in milliliters per hour (mL/hr). In other embodiments, the flow rate indicator 62 may be programmed to indicate other different flow rates.

In one embodiment, the flow rate indicator 62 includes a first LED element 64 and a second LED element 66, as will be described in more detail below. Referring to FIG. 1, the infusion pump 18 includes a power button 68 and a flow rate selector button 70. In one embodiment, the power button 68 is used to turn the infusion pump 18 on and off, and to initiate the infusion pump 18 to activate. The flow rate selector button 70 is used to toggle and select a desired flow rate of the fluid 16 through the infusion pump 18 and the medical infusion system 10.

Figure 8:
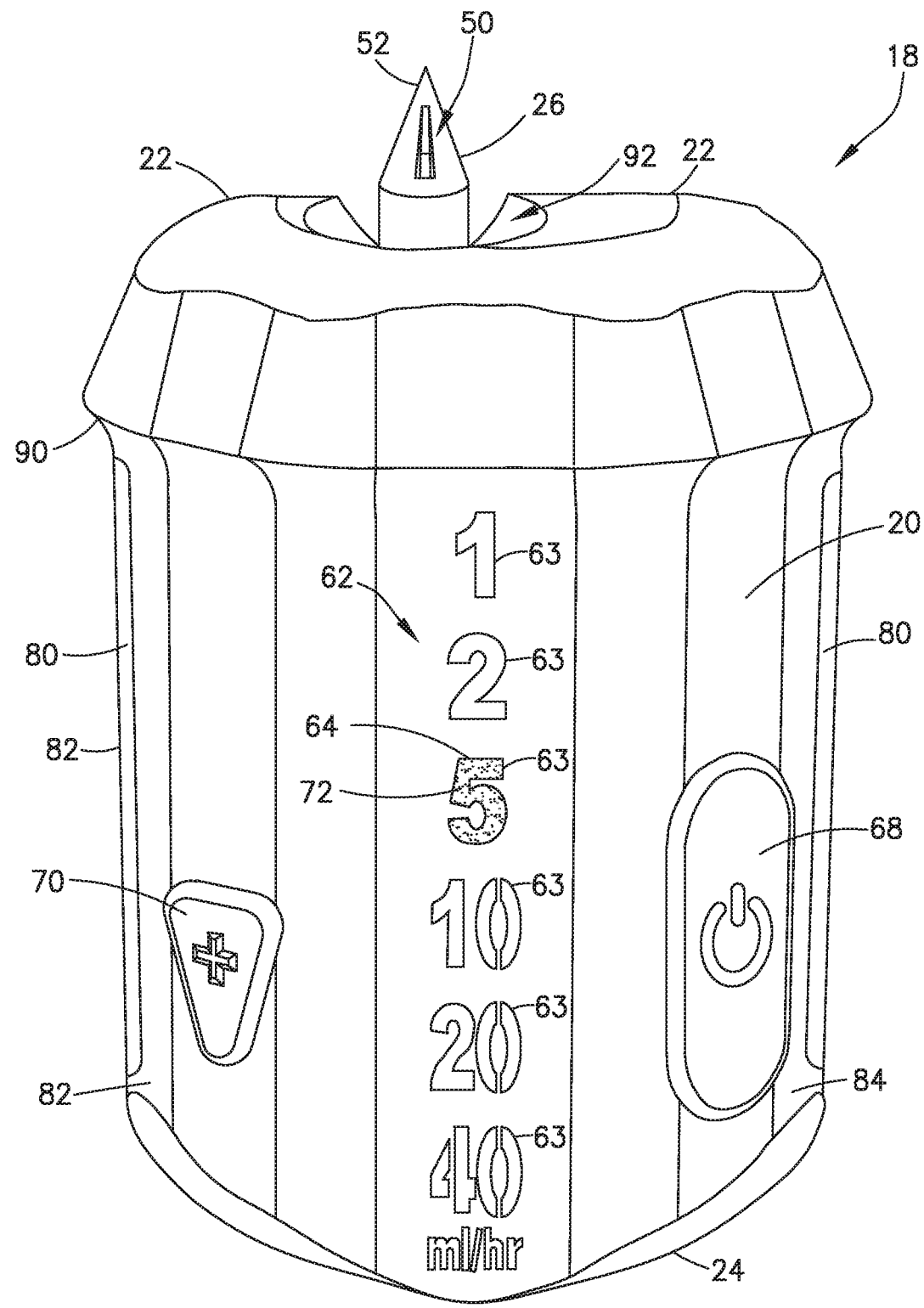
FIG. 8 is a front perspective view of an infusion pump with a first LED element of a selected flow rate element activated and providing a first visual indication in accordance with an embodiment of the present invention.

During use, when a patient or a medical practitioner uses the flow rate selector button 70 to select a flow rate of the fluid 16, the selected flow rate element 63 representing the selected flow rate number lights up. For example, each flow rate element 63 includes a first LED element 64 and a second LED element 66. Referring to FIG. 8, the first LED element 64 of the selected flow rate element 63 is activated when that flow rate element 63 is selected using the flow rate selector button 70. The first LED element 64 provides a first visual indication 72. For example, the first LED element 64 may provide a blue light that illuminates the selected flow rate element 63. In this manner, a patient or a medical practitioner receives a visual indication, e.g., the blue light, of which flow rate element 63 has been selected.

In one embodiment, the infusion pump 18 includes an alarm system for detecting air within the infusion pump 18. In an exemplary embodiment, the alarm system includes a sensor, e.g., a bubble sensor 302, that detects a presence of air within the infusion pump 18. When the bubble sensor 302 detects the presence of air, the second LED element 66 is activated. For example, in one embodiment, when the alarm system is activated, the second LED element 66 of each flow rate element 63 is activated. The second LED element 66 provides a second visual indication 74 different than the first visual indication 72. For example, the second LED element 66 may provide a flashing red light that illuminates each of the flow rate elements 63. In one embodiment, the bubble sensor 302 may include additional mechanisms for detecting and removing the presence of air.

Figure 9:
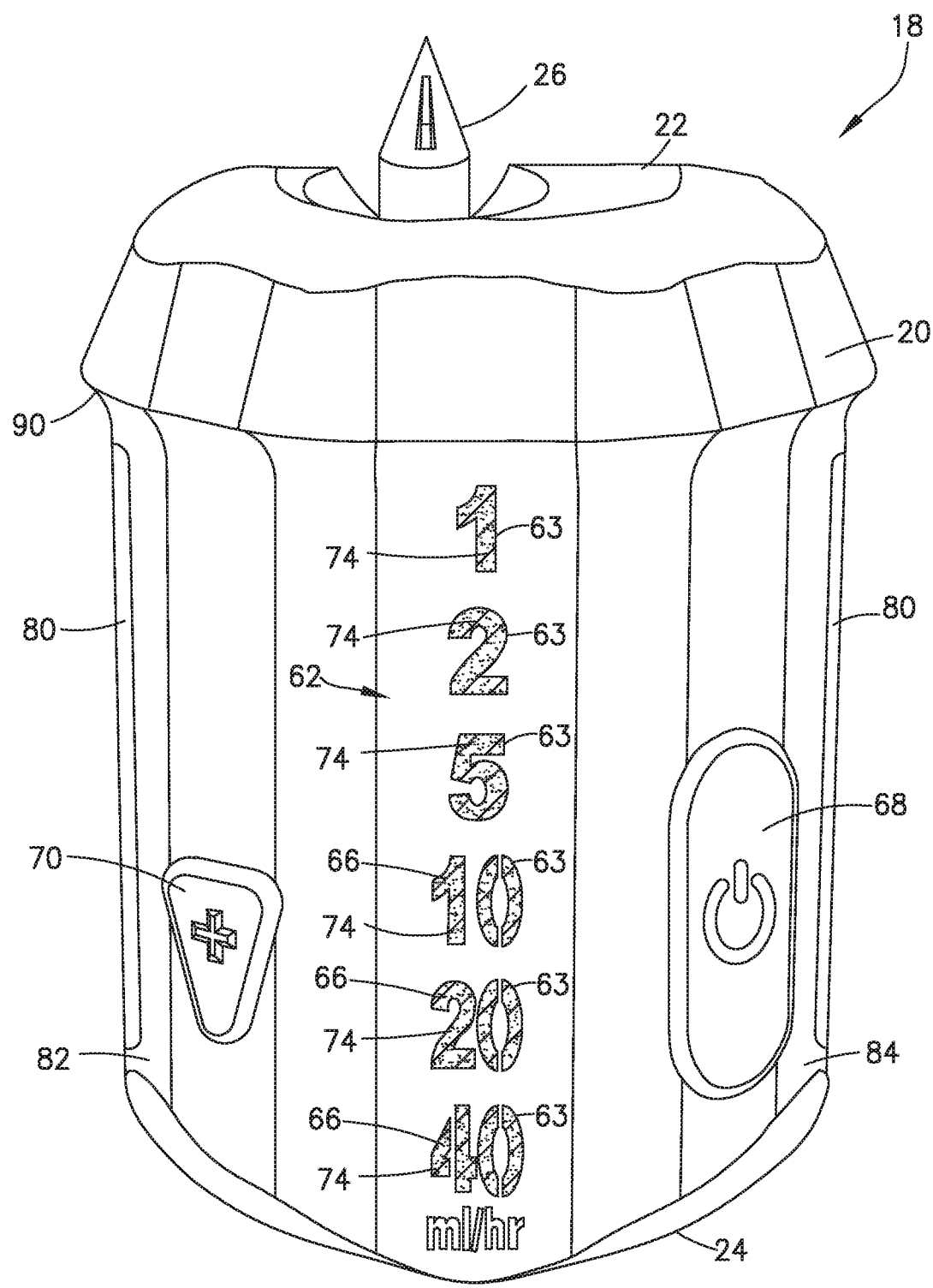
FIG. 9 is a front perspective view of an infusion pump with a second LED element of each flow rate element activated and providing a second visual indication in accordance with an embodiment of the present invention.

Referring to FIG. 9, when the alarm system is activated, the second LED element 66 of each flow rate element 63 is activated, and each flow rate element 63 provides a flashing red light. In this manner, a patient or a medical practitioner receives a visual indication, e.g., the flashing red light, which indicates that the alarm system has been activated and the presence of air has been detected within the medical infusion system 10. In one embodiment, activation of the alarm system will also automatically shut the infusion pump 18 off. A medical practitioner may then remove the air within the system 10 before restarting the infusion pump 18. It is also contemplated that in some embodiments, activation of the alarm system will also start an automatic air removal component allowing for automatic removal of the air from the system 10.

In one embodiment, the alarm system may be activated for the presence of air and/or for occlusion, i.e., an increase of pressure at the inlet end 22 or the outlet end 24 of the infusion pump 18. For example, the infusion pump 18 may include one or more pressure sensors 304.

Figure 10:
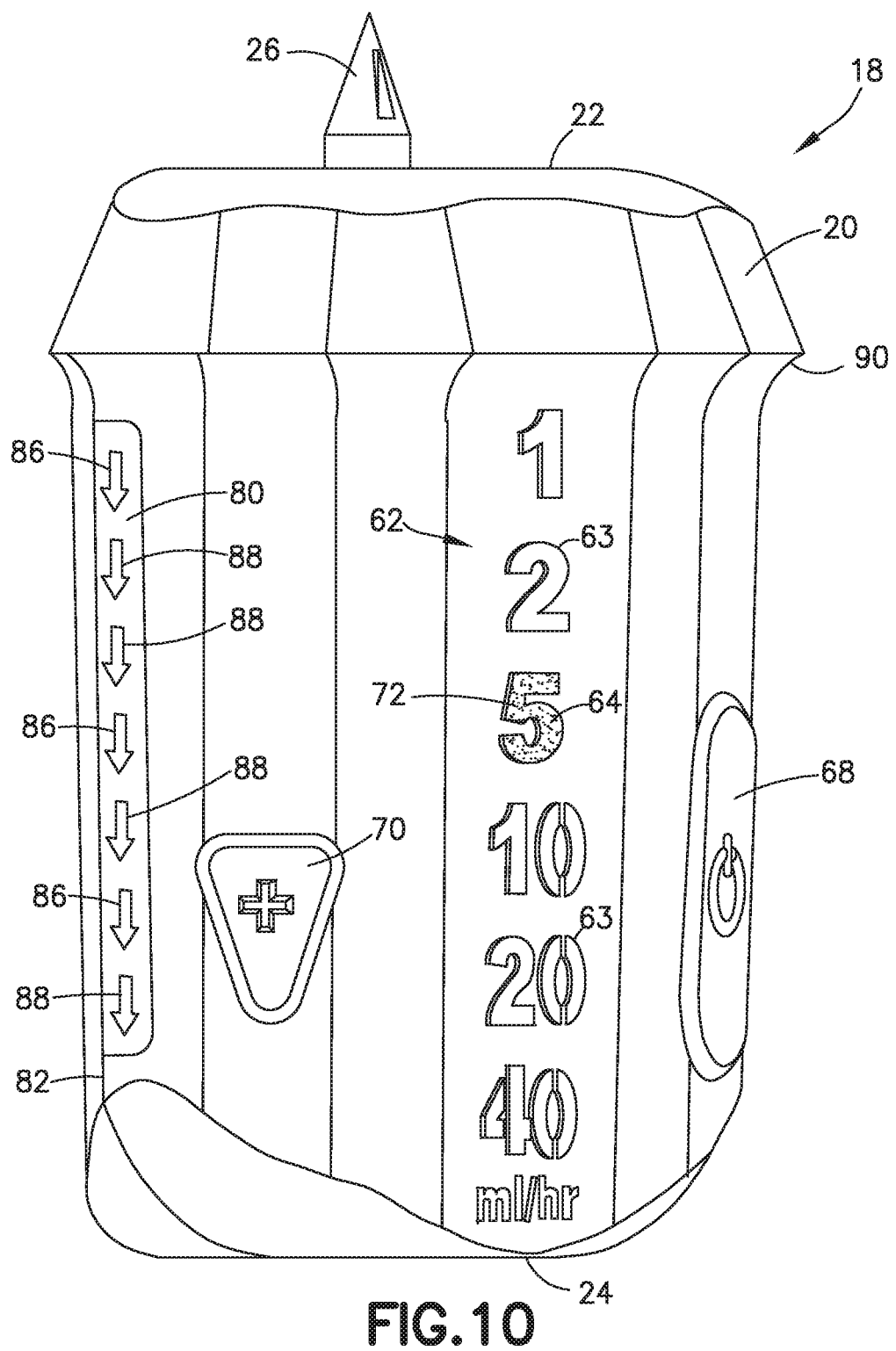
FIG. 10 is a side perspective view of an infusion pump with a scrolling LED element activated in accordance with an embodiment of the present invention.

Referring to FIG. 10, the housing 20 of the infusion pump 18 includes a scrolling light bar 80 spanning a portion of the infusion pump 18. For example, a first side portion 82 of the housing 20 of the infusion pump 18 may include a light bar 80. Referring to FIG. 1, in one embodiment, a first side portion 82 and a second side portion 84 of the housing 20 of the infusion pump 18 may each include a light bar 80. A light bar 80 of the present disclosure includes a scrolling LED element 86. In one embodiment, the scrolling LED element 86 is activated when the infusion pump 18 is running, i.e., when the power button 68 is pressed to initiate the infusion pump 18 to activate, and a fluid 16 to be pumped through the system 10, the scrolling LED element 86 is activated. Referring to FIG. 10, the scrolling LED element 86 includes a plurality of arrows 88 scrolling downward to provide a visual indication to a patient or a medical practitioner that infusion is occurring, e.g., a fluid 16 is being pumped from an intravenous fluid container 12 to a patient's intravenous port via the infusion pump 18 and the flexible tubing 32.

Figure 2:
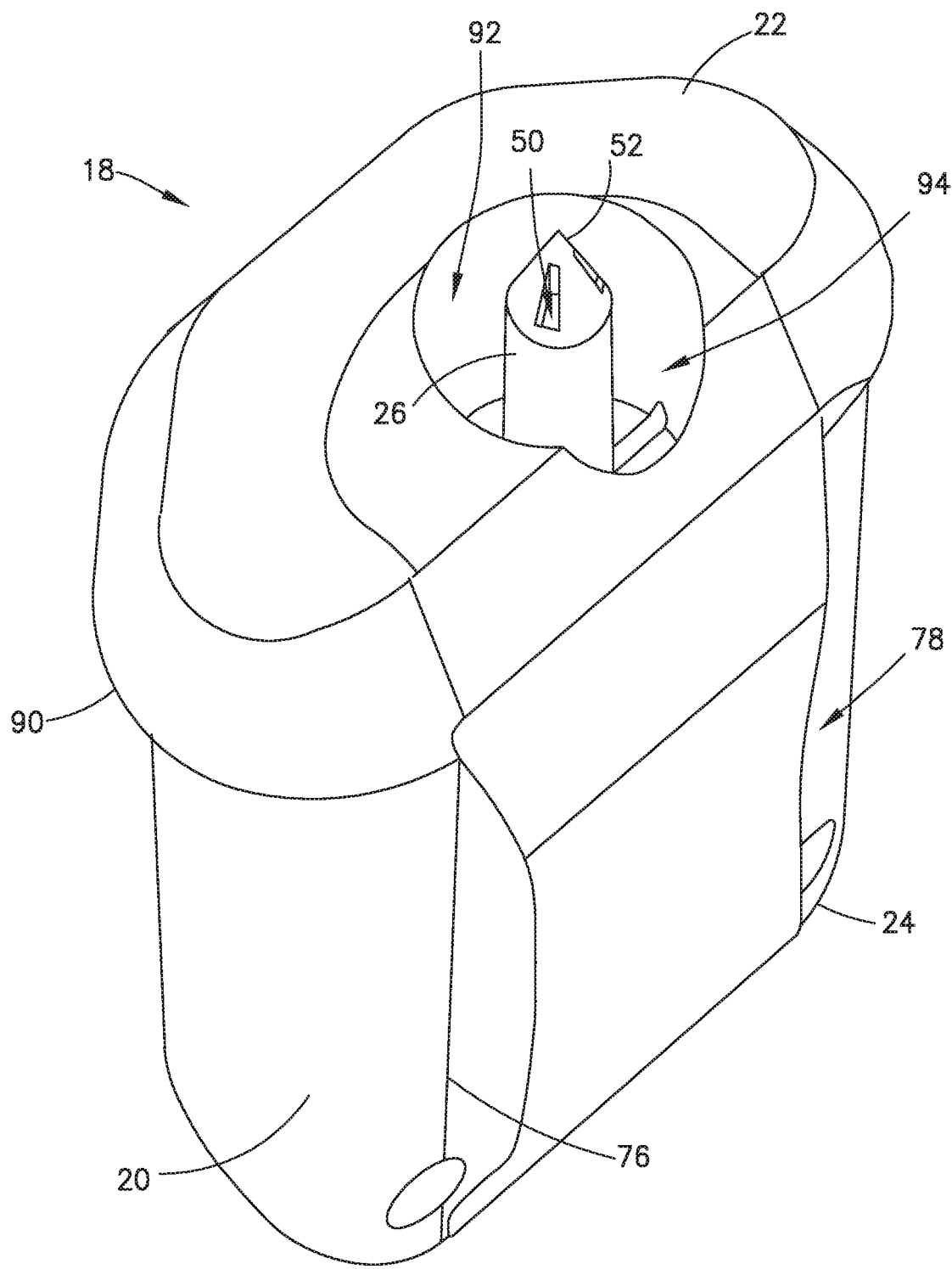
FIG. 2 is a rear perspective view of an infusion pump in accordance with an embodiment of the present invention.
Figure 3A:
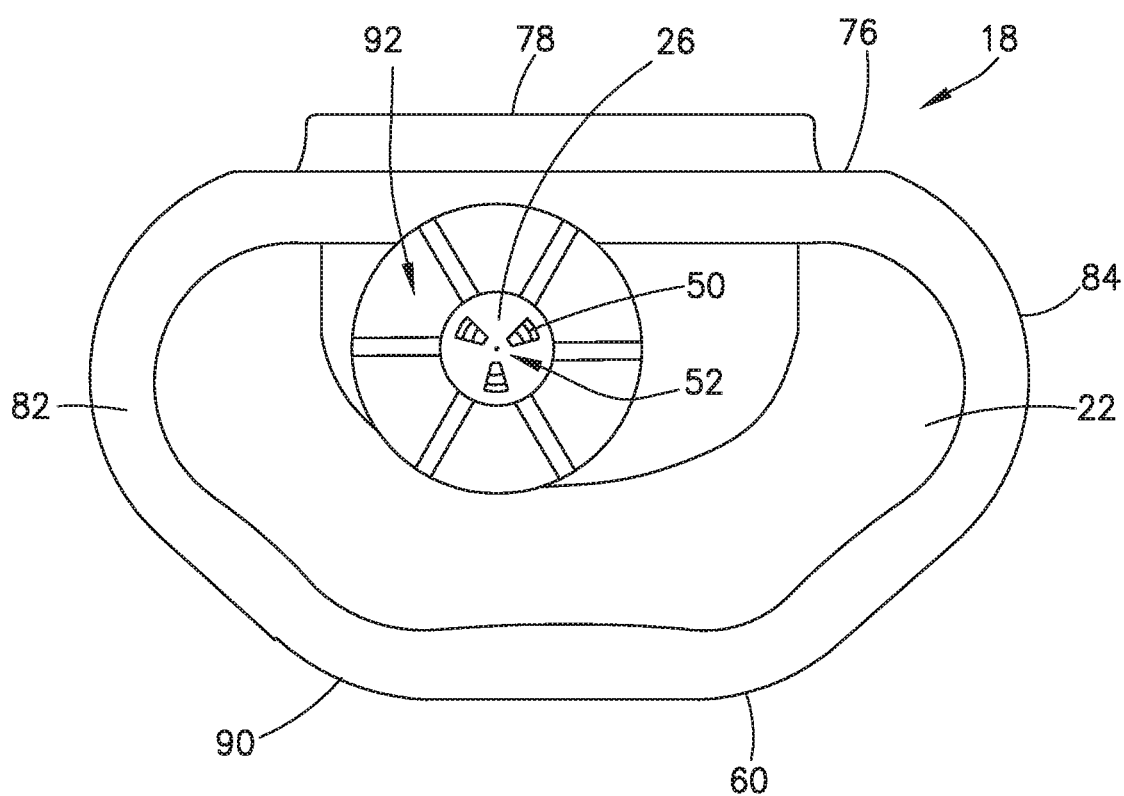
FIG. 3A is a top perspective view of an infusion pump in accordance with an embodiment of the present invention.
Figure 3B:
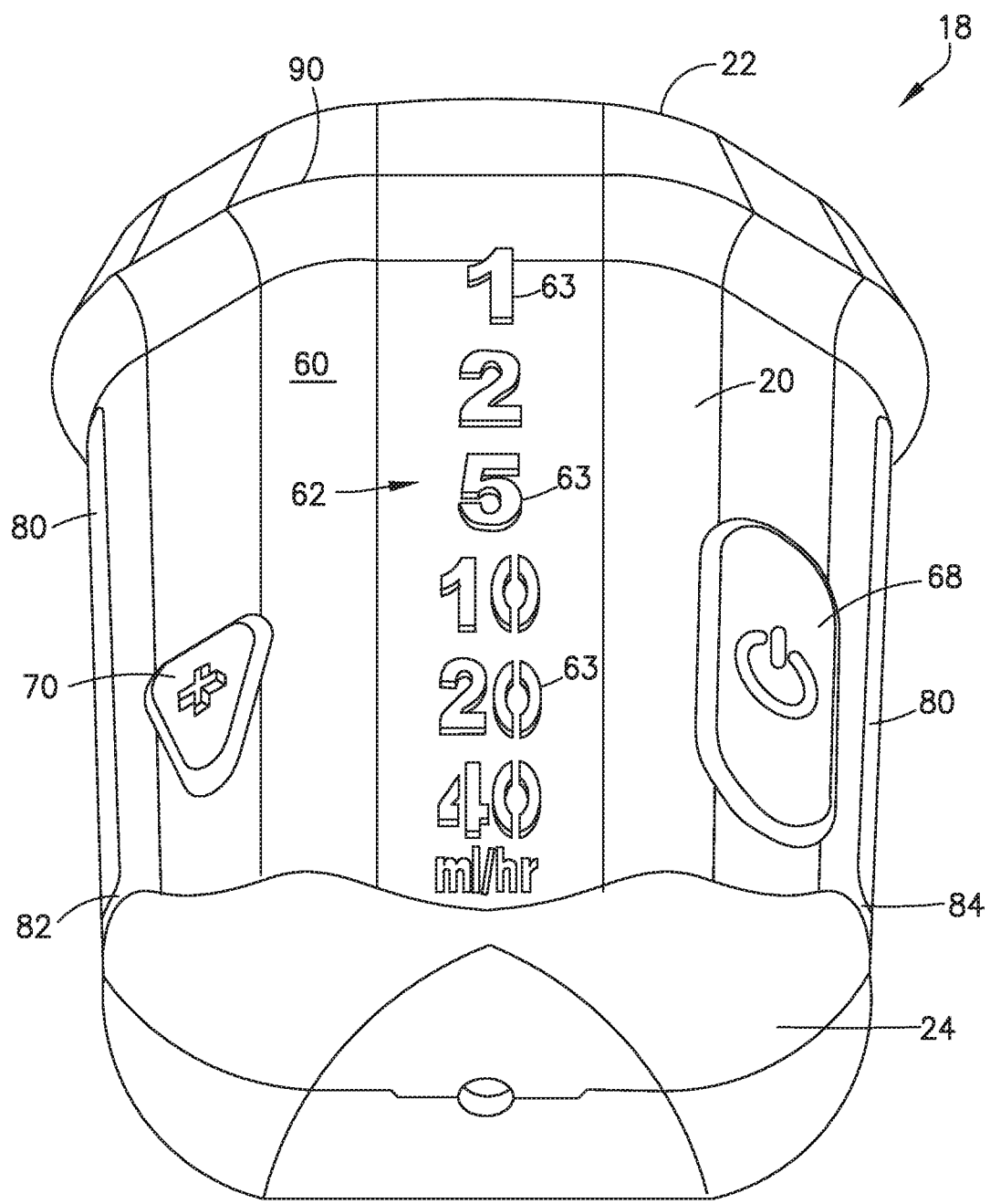
FIG. 3B is a bottom perspective view of an infusion pump in accordance with an embodiment of the present invention.
Figure 4:
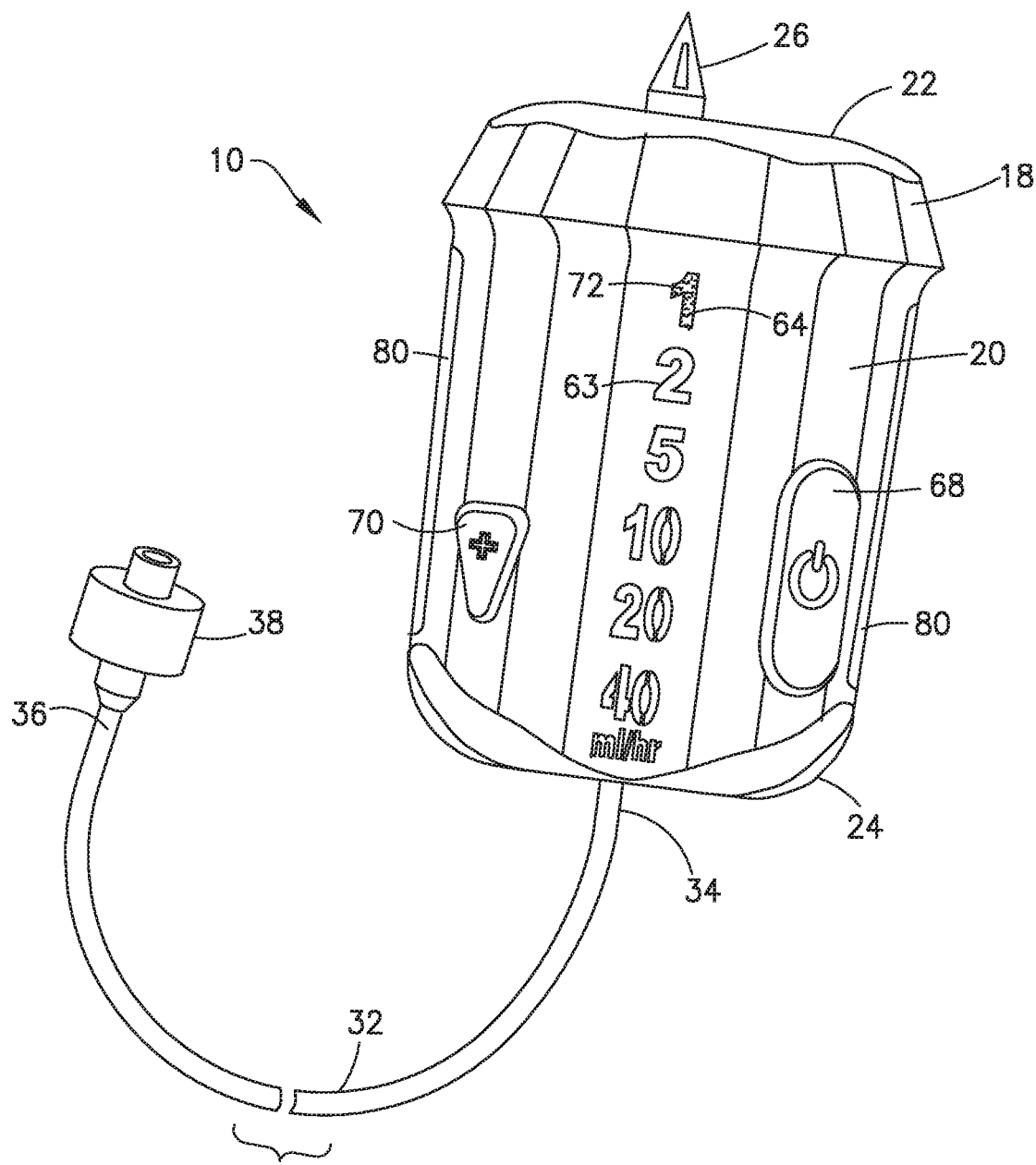
FIG. 4 is a front perspective view of an infusion pump and flexible tubing in accordance with an embodiment of the present invention.

Referring to FIG. 2, the infusion pump 18 includes a strap receiving loop 78. In one embodiment, a back portion 76 of the infusion pump 18 includes the strap receiving loop 78. In other embodiments, other portions of the infusion pump 18 may include the strap receiving loop 78. A carrying strap, e.g., a carrying strap 40 (FIG. 7A), can be placed through the strap receiving loop 78 so that a patient is able to wear the infusion pump 18 on their arm, or other convenient location, via the carrying strap.

Referring to FIGS. 1-4 and 10, the housing 20 of the infusion pump 18 includes a finger grasping lip portion 90 adjacent the first end 22 of the housing 20. The lip portion 90 provides structure that a patient or a medical practitioner can grasp with fingers to better hold the housing 20 of the infusion pump 18 when connecting the spike member 26 to the injection port 14 of the intravenous fluid container 12.

Referring to FIGS. 1-3A, the first end 22 of the housing 20 of the infusion pump 18 includes a recessed portion 92 and a viewing window 94. Referring to FIGS. 1-3A, a portion of the spike member 26 is disposed within the recessed portion 92. In this manner, an overall size and profile of the infusion pump 18 is reduced. For example, an infusion pump 18 of the present disclosure allows for a portion of the spike member 26 to be disposed within the recessed portion 92, thereby reducing a distance that the spike member 26 extends from the first end 22 of the housing of the infusion pump 18.

The viewing window 94 of the housing 20 allows a patient or a medical practitioner an area to visualize when a spike member 26 is properly connected with the injection port 14 of the intravenous fluid container 12. This helps a patient or a medical practitioner to receive visual feedback when the spike member 26 is properly connected with the injection port 14 of the intravenous fluid container 12.

Referring to FIGS. 1-7A, 7C-10, and 14, use of a medical infusion system 10 of the present disclosure will now be described.

Referring to FIGS. 6A and 6B, when an intravenous infusion is needed, a patient or a medical practitioner is able to spike or pierce a fluid barrier member 110 of an injection port 14 of intravenous fluid container 12 with puncturing point 52 of spike member 26 of infusion pump 18 and securely connect spike member 26 to injection port 14 of intravenous fluid container 12. Advantageously, spike member 26 is locked and anchored within injection port 14, i.e., significant relative movement between spike member 26 of infusion pump 18 and injection port 14 of intravenous fluid container 12 is prevented and disconnection of spike member 26 of infusion pump 18 from the injection port 14 of intravenous fluid container 12 is prevented.

Next, the fitting 38 of flexible tubing 32 is connected to a patient's intravenous port or a patient's catheter for an infusion transfer of the fluid 16 from the intravenous fluid container 12 to the patient via the infusion pump 18.

Advantageously, a patient or a medical practitioner is able to use the flow rate selector button 70 of the infusion pump 18 to select a flow rate of the fluid 16. Referring to FIG. 8, a selected flow rate element 63 representing the selected flow rate number lights up so that a patient or a medical practitioner receives a visual indication, e.g., a blue light, of which flow rate element 63 has been selected.

If desired, a patient or a medical practitioner is able to use the flow rate selector button 70 during an infusion to change the flow rate of the fluid 16. Also, if desired, a patient or a medical practitioner is able to use the power button 68 to start and stop the infusion of the fluid 16.

Once an infusion procedure is complete, a patient or a medical practitioner may throw everything out, e.g., a medical infusion system 10 of the present disclosure is disposable. For example, in one embodiment, all of the components of a medical infusion system 10 are disposable, i.e., the system 10 is fully disposable. In another embodiment, a medical infusion system 10 is partially disposable, i.e., a portion of the infusion pump 18 that contains a battery 312 and an electronic circuit board 300 is able to be removed from the infusion pump 18 and reused. The other components of the medical infusion system 10 are then able to be disposed of.

Figure 11:
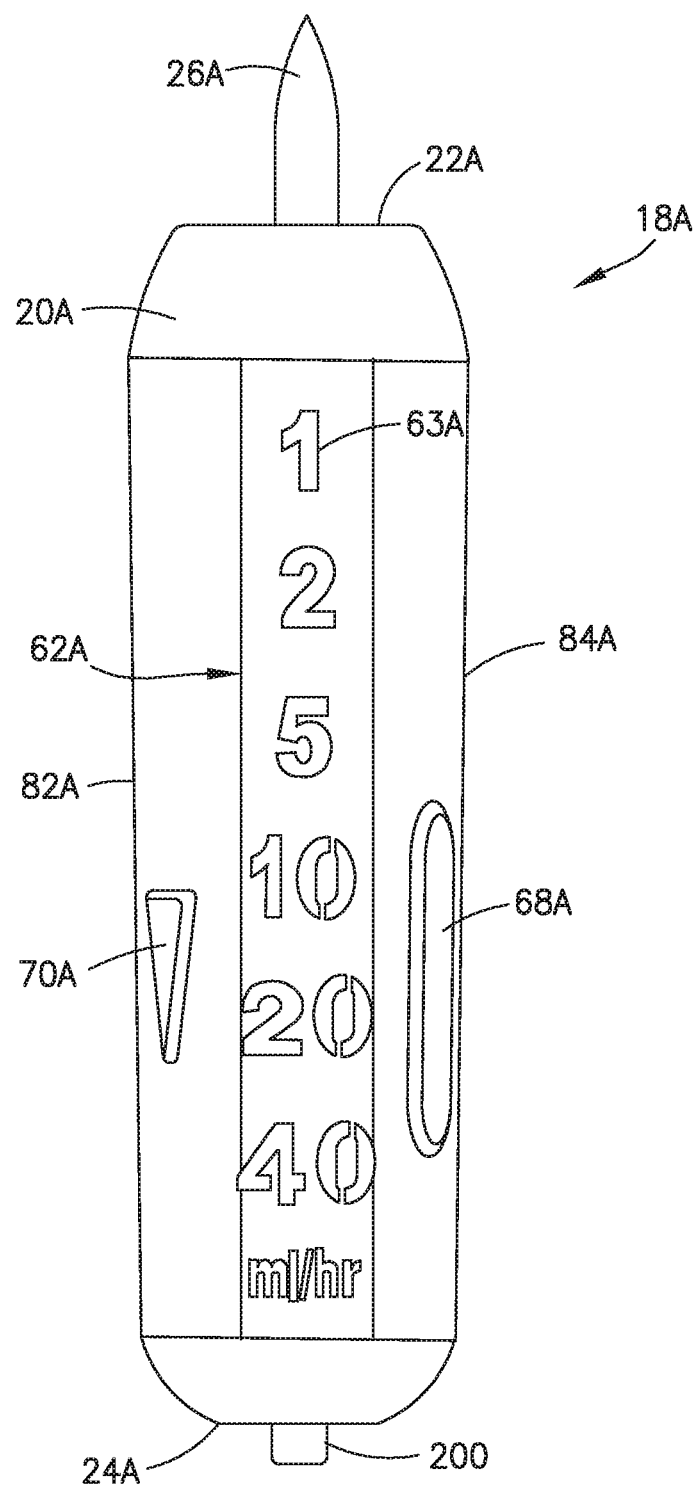
FIG. 11 is a front perspective view of an infusion pump in accordance with another embodiment of the present invention.
Figure 12:
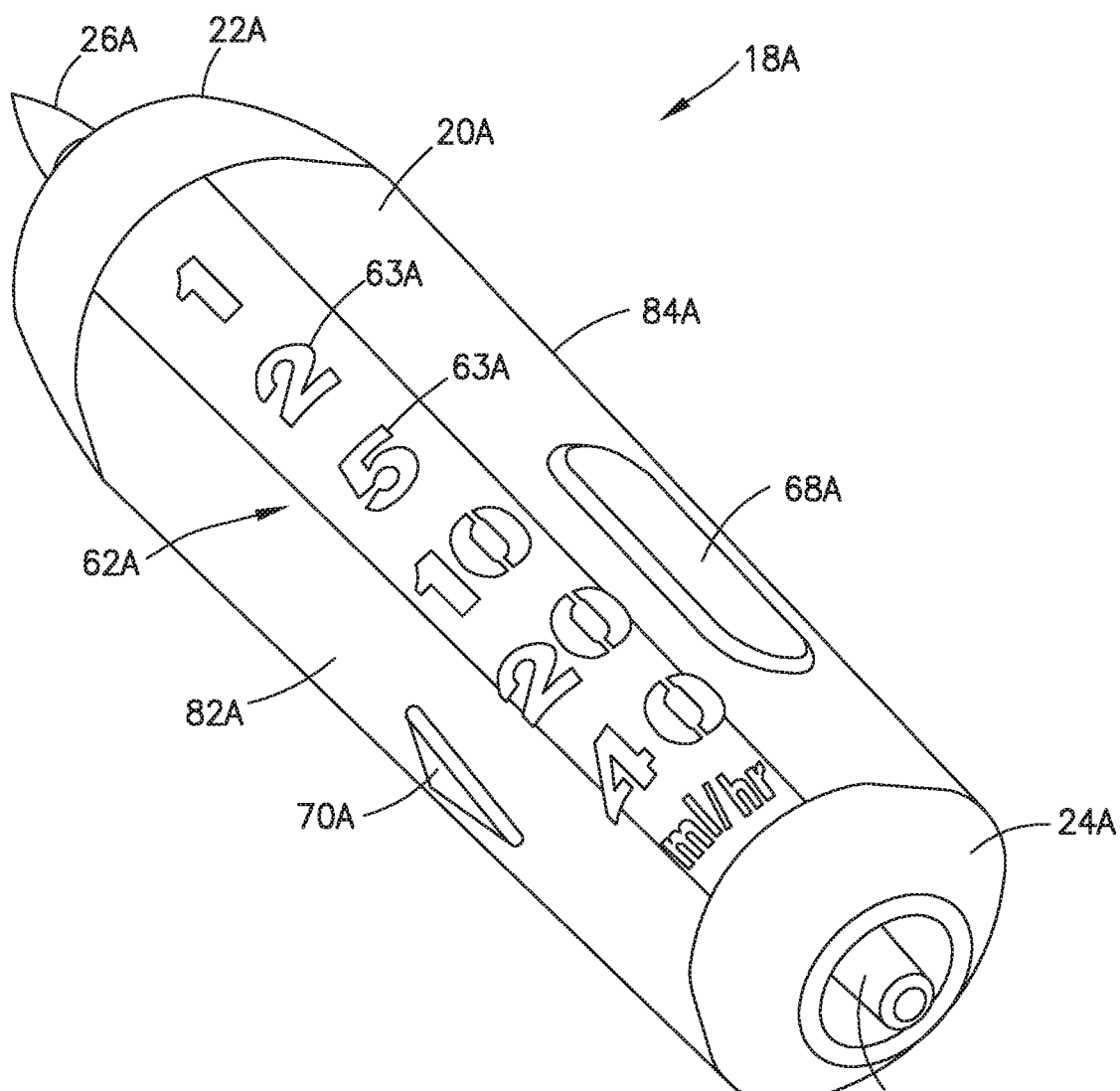
FIG. 12 is a bottom perspective view of an infusion pump in accordance with another embodiment of the present invention.
Figure 13:
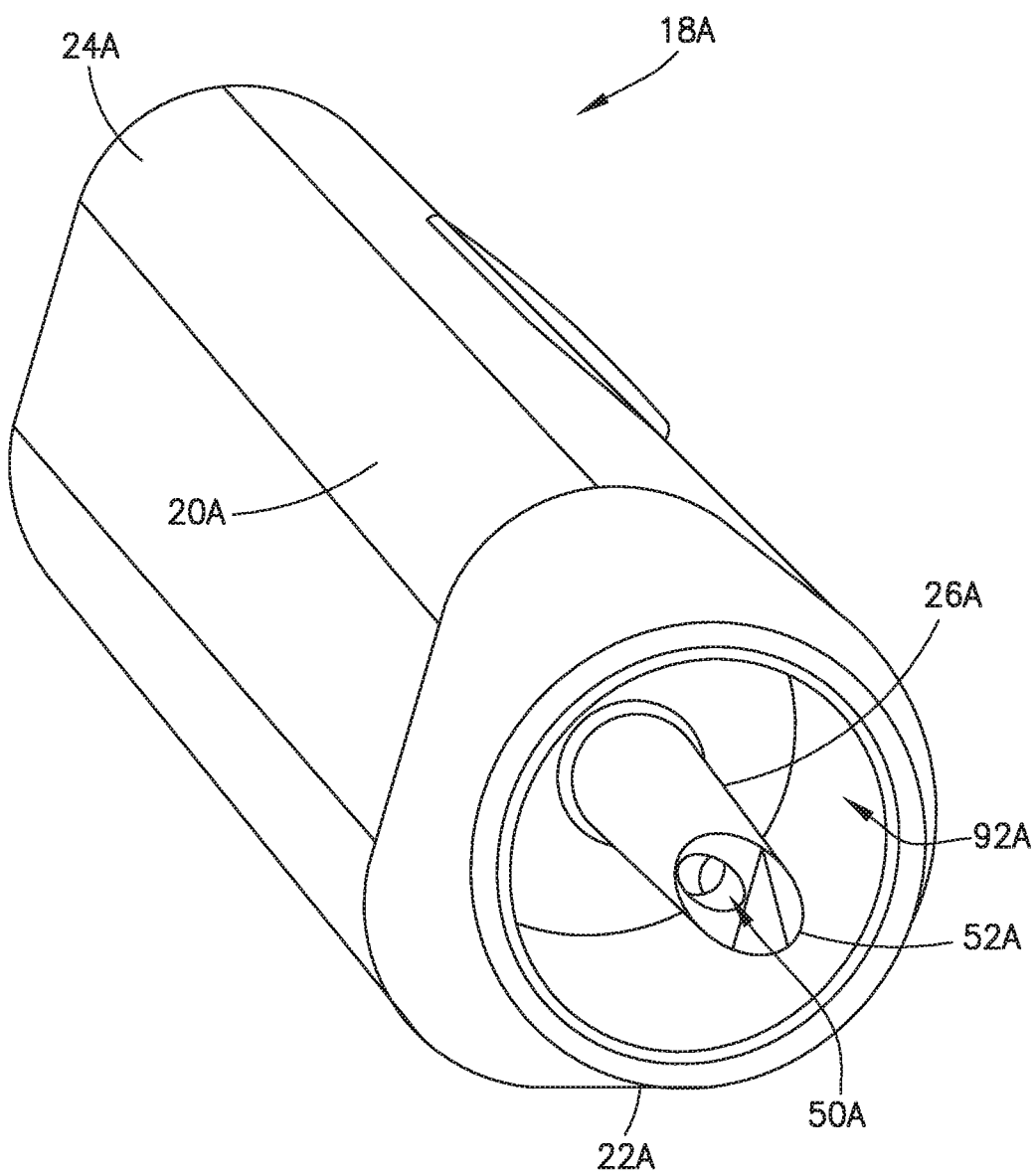
FIG. 13 is a top perspective view of an infusion pump in accordance with another embodiment of the present invention.

FIGS. 11-13 illustrate another exemplary embodiment of an infusion pump of the present disclosure. The embodiment illustrated in FIGS. 11-13 includes similar components to the embodiment illustrated in FIGS. 1-7A, 7C-10, and 14, and the similar components are denoted by a reference number followed by the letter A. For the sake of brevity, these similar components and the similar steps of using infusion pump 18A (FIGS. 11-13) will not all be discussed in conjunction with the embodiment illustrated in FIGS. 11-13.

Referring to FIGS. 11-13, infusion pump 18A defines a cylindrical shape. The infusion pump 18A includes a Luer lock connector 200 for removably connecting with a first end 34 of a flexible tubing 32.

The infusion pump allows a user to selectively control a flow rate of a fluid and includes a spike member that is connectable to an injection port of an intravenous fluid container.

The infusion pump of the present disclosure replaces a drip chamber in a conventional intravenous (V) set. Advantageously, integrating an infusion pump of the present disclosure into an IV set increases a patient's mobility while receiving an IV. Early ambulation after a hospital procedure is known to have many benefits and contributes to improved patient outcomes. By having an infusion pump of the present disclosure integrated into an IV set, a patient can be freed from the burden of bringing an IV pole along with them as they ambulate. Common infusions are gravity based, and thus a patient is required to be close to the IV pole for the duration of the infusion. An infusion pump of the present disclosure allows a patient to be able to wear a small IV bag on their arm for example, or carry the IV bag and pump in a small backpack. The active fluid delivery the infusion pump of the present disclosure provides allows for orientation independence, i.e., the system is not in any way dependent on gravity for the delivery of fluid, so the bag need not be above the pump or the patient's catheter. The patient could wear the bag on an arm, and freely lie down or get up and walk around with no interruption in the infusion. In this manner, a patient would be free to move about unencumbered by an IV pole.

A medical infusion system 10 of the present disclosure provides a standalone intravenous fluid administration system and a lower cost solution than conventional intravenous fluid administration systems. The low cost of a medical infusion system 10 of the present disclosure enables a disposable system 10 and/or infusion pump 18. The system 10 and/or infusion pump 18 being disposable eliminates cleaning, sterilizing, and tracking costs associated with conventional systems.

The simplified interface of the infusion pump 18 of the present disclosure allows the clinician's workflow to be streamlined and the potential for medication errors to be reduced.

An alternative embodiment of a medical infusion system of the present disclosure could include special features for accommodating delivery of hazardous drugs such as chemotherapeutics. It is contemplated that alternative embodiments could incorporate closed system transfer device (CSTD) components for hazardous drug delivery. For example, CSTD connectors may be provided at the first end 22 and the second end 24 of the infusion pump 18. It is also contemplated that the infusion pump 18 could be attached to the injection port 14 of the intravenous fluid container 12 in the pharmacy and the infusion pump 18 used to fill the intravenous fluid container 12 during compounding of the medication. In this manner, overall usage of the disposable CSTD components during compounding and administration of the medication may be reduced.

It is also contemplated that the system of the present disclosure could include an integrated internal reservoir that is filled at the pharmacy or by a clinician. Alternatively, a custom cartridge could be used, either pre-filled or filled at the pharmacy or on a hospital floor. Such devices would be useful regardless of the source of infusate, and could facilitate technologies branching out beyond a traditional intravenous bag.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An infusion device for delivery of a fluid, comprising:
   a housing having an inlet and an outlet;
   a spike member at the inlet, the spike member defining a portion of a fluid channel, the fluid channel in fluid communication with the inlet and the outlet;
   a pump for pumping the fluid through the spike member and out the outlet of the housing that operates at a plurality of predetermined discrete flow rate values;
   a plurality of flow rate indicator elements that indicate a selected flow rate value for the pump of the plurality of predetermined discrete flow rate values, each flow rate indicator element comprising a first LED element and a second LED element, wherein each of the plurality of flow rate indicator elements is representative of one of the plurality of predetermined discrete flow rate values of the pump; and
   a controller in communication with the pump and with the plurality of flow rate indicator elements, wherein the controller selectively controls the pump to operate at one of the plurality of predetermined discrete flow rate values, selectively activates the first LED element of one of the plurality of flow rate indicator elements representative of the selected flow rate value for the pump to provide a first visual indication for the selected flow rate value for the pump, and simultaneously activates the second LED elements of the plurality of flow rate indicator elements to provide a second visual indication that indicates a device alarm.

2. The infusion device of claim 1, further comprising a flow rate selector button that allows a user to select the flow rate of the fluid from the plurality of predetermined discrete flow rate values represented by the plurality of flow rate indicator elements.

3. The infusion device of claim 1, further comprising a light bar, wherein the light bar includes a third LED element comprising a scrolling LED element that is activated by the controller when a power button of the infusion device is pressed and the fluid is moving through the pump.

4. The infusion device of claim 1, wherein the inlet of the housing includes a recessed portion, wherein a portion of the spike member is disposed within the recessed portion.

5. The infusion device of claim 1, wherein the spike member is connectable to an injection port of an intravenous fluid container.

6. The infusion device of claim 1, wherein the plurality of predetermined discrete flow rate values are not separated by an equal flow rate amount.

7. The infusion device of claim 1, wherein the plurality of predetermined discrete flow rate values comprise at least a first flow rate value, a second flow rate value, and a third flow rate value, and wherein a difference between the first flow rate value and the second flow rate value is less than a difference between the second flow rate value and the third flow rate value.

8. The infusion device of claim 1, wherein the plurality of predetermined discrete flow rate values comprise flow rates of 1 mL/hr, 2 mL/hr, 5 mL/hr, 10 mL/hr, 20 mL/hr, and 40 mL/hr.

9. The infusion device of claim 1, wherein the plurality of flow rate indicator elements comprise numerals for the plurality of predetermined discrete flow rate values that are illuminated when the flow rate indicator element is activated.

10. The infusion device of claim 1, wherein the pump comprises at least one of a rotary pump, a brushed direct current (DC) electric motor, a brushless motor, a stepper motor, a servomotor, a gear motor, a hollow shaft motor, a shaftless motor, or a diaphragm pump.

11. The infusion device of claim 1, further comprising flexible tubing extending through the outlet of the housing, the flexible tubing comprising a first end connected to the pump and a second end outside of the housing comprising a connector configured to be connected to an intravenous port.

12. The infusion device of claim 11, further comprising an alarm system comprising a bubble sensor connected to the flexible tubing, wherein the bubble sensor is configured to detect a presence of air within the flexible tubing and, if the presence of air is detected, the alarm system is configured to cause the controller to provide the second visual indication to a user.

13. A medical infusion system, comprising:
an intravenous fluid container having an injection port; and
an infusion device for delivery of a fluid, comprising:
a housing having an inlet and an outlet;
a spike member at the inlet, the spike member defining a portion of a fluid channel, the fluid channel in fluid communication with the inlet and the outlet;
a pump for pumping the fluid through the spike member and out the outlet of the housing that operates at a plurality of predetermined discrete flow rate values;
a plurality of flow rate indicator elements that indicate a selected flow rate value for the pump of the plurality of predetermined discrete flow rate values, each flow rate indicator element comprising a first LED element and a second LED element, wherein each of the plurality of flow rate indicator elements is representative of one of the plurality of predetermined discrete flow rate values of the pump; and
a controller in communication with the pump and with the plurality of flow rate indicator elements,
wherein the controller selectively controls the pump to operate at one of the plurality of predetermined discrete flow rate values and selectively activates the first LED element of one of the plurality of flow rate indicator elements representative of the selected flow rate value for the pump to provide a first visual indication representative of the selected flow rate value for the pump,
wherein the second LED elements of the plurality of flow rate indicator elements are activated simultaneously by the controller providing a second visual indication that indicates a device alarm, and
wherein the spike member is connectable to the injection port.

14. The medical infusion system of claim 13, wherein the infusion device further comprises an alarm system comprising a bubble sensor configured to detect a presence of air within the infusion device and, if the presence of air is detected, the alarm system is configured to cause the controller to provide the second visual indication that indicates the device alarm.

15. The medical infusion system of claim 13, wherein the infusion device further comprises a flow rate selector button that allows a user to select the flow rate of the fluid from the plurality of predetermined discrete flow rate values represented by the plurality of flow rate indicator elements.

16. The medical infusion system of claim 13, wherein the spike member of the infusion device is directly connected to the injection port of the intravenous fluid container containing the fluid to be delivered to a patient, and
wherein the infusion device and the intravenous fluid container are configured to be worn by the patient as the fluid is delivered to the patient.

17. The medical infusion system of claim 16, further comprising a carrying strap attached to the intravenous fluid container configured to secure the intravenous fluid container to an arm of the patient.

18. An infusion device for delivery of a fluid, comprising:
a housing having an inlet and an outlet;
a spike member at the inlet, the spike member defining a portion of a fluid channel, the fluid channel in fluid communication with the inlet and the outlet;
a pump for pumping the fluid through the spike member and out the outlet of the housing that operates at a plurality of predetermined discrete flow rate values;
a plurality of flow rate indicator elements that indicate a selected flow rate value for the pump of the plurality of predetermined discrete flow rate values, wherein each of the plurality of flow rate indicator elements is representative of one of the plurality of predetermined discrete flow rate values of the pump;
flexible tubing extending through the outlet of the housing, the flexible tubing comprising a first end connected to the pump and a second end outside of the housing comprising a connector configured to be connected to an intravenous port;
a controller in communication with the pump and with the plurality of flow rate indicator elements; and
an alarm system comprising a bubble sensor connected to the flexible tubing,
wherein the controller selectively controls the pump to operate at one of the plurality of predetermined discrete flow rate values and activates one of the plurality of flow rate indicator elements representative of the selected flow rate value for the pump, and
wherein the bubble sensor is configured to detect a presence of air within the flexible tubing and, if the presence of air is detected, the alarm system is configured to activate all of the plurality of flow rate indicator elements simultaneously.

\* \* \* \* \*